US009642541B2

(12) United States Patent
Sawanoi

(10) Patent No.: US 9,642,541 B2
(45) Date of Patent: May 9, 2017

(54) BLOOD PRESSURE MEASUREMENT DEVICE

(71) Applicant: Yukiya Sawanoi, Nara (JP)

(72) Inventor: Yukiya Sawanoi, Nara (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 856 days.

(21) Appl. No.: 13/746,638

(22) Filed: Jan. 22, 2013

(65) Prior Publication Data

US 2014/0207009 A1  Jul. 24, 2014

(30) Foreign Application Priority Data

Jan. 23, 2012  (JP) ................................ 2012-010924

(51) Int. Cl.
*A61B 5/022*  (2006.01)
*A61B 5/00*  (2006.01)
(Continued)

(52) U.S. Cl.
CPC ...... *A61B 5/02225* (2013.01); *A61B 5/02208* (2013.01); *A61B 5/02233* (2013.01);
(Continued)

(58) Field of Classification Search
CPC ..... A61B 5/021; A61B 5/022; A61B 5/02208; A61B 5/02225; A61B 5/02233;
(Continued)

(56) References Cited

U.S. PATENT DOCUMENTS 4,660,567 A * 4/1987 Kaneko et al. ............... 600/495
5,135,003 A * 8/1992 Souma ............... A61B 5/02208
600/493

(Continued)

FOREIGN PATENT DOCUMENTS

JP        62-268532 A     11/1987
JP     2005-304670 A     11/2005
(Continued)

OTHER PUBLICATIONS

Bordley et al. "Recommendations for human blood pressure determinations by sphygmomanometers." Circulation. Oct. 4, 1951(4):503-9.*

(Continued)

*Primary Examiner* — Meredith Weare
(74) *Attorney, Agent, or Firm* — Osha Liang LLP

(57) ABSTRACT

A blood pressure measurement device corrects the error caused by blood congestion. The device includes a blood pressure measurement section that calculates a blood pressure value of a patient based on the cuff pressure and pulse waves detected by a pressure sensor, a blood congestion determination section that determines a degree of blood congestion that occurred at a peripheral side of the measurement location due to the cuff pressure on the measurement location in accordance with a predetermined method, a blood pressure correction section that calculates a corrected blood pressure value based on the degree of the blood congestion, and a display that displays the corrected blood pressure value.

2 Claims, 14 Drawing Sheets

(51) Int. Cl.
*A61B 7/00* (2006.01)
*A61B 7/04* (2006.01)

(52) U.S. Cl.
CPC ............ *A61B 5/7278* (2013.01); *A61B 5/742* (2013.01); *A61B 7/00* (2013.01); *A61B 7/045* (2013.01)

(58) Field of Classification Search
CPC ............ A61B 5/02241; A61B 5/0225; A61B 5/02255; A61B 5/023; A61B 5/0235
See application file for complete search history.

(56) References Cited

U.S. PATENT DOCUMENTS 5,993,396 A * 11/1999 Friedman et al. ............ 600/490
8,764,670 B2 * 7/2014 Sawanoi et al. ............ 600/490
2005/0234350 A1 * 10/2005 Sawanoi ................ A61B 5/022 600/490
2011/0021927 A1 * 1/2011 Sawanoi ............ A61B 5/02255 600/479
2011/0208070 A1 * 8/2011 Sawanoi et al. ............ 600/493
2011/0257538 A1 * 10/2011 Sawanoi ....................... 600/490
2011/0257540 A1 * 10/2011 Sawanoi ................ G01G 19/50 600/494

FOREIGN PATENT DOCUMENTS

WO  WO-2010073688 A1 * 7/2010 ............. G01G 19/50
WO  WO 2011/055717 A1 * 5/2011 ............. A61B 5/022

OTHER PUBLICATIONS

Office Action in counterpart Japanese Patent Application No. 2012-010924, mailed Sep. 8, 2015 (7 pages).

* cited by examiner

FIG. 4

| ID | Measurement Date and Time | Degree of Blood Congestion | Estimated Systolic Blood Pressure | Blood Pressure Value and Pulse Rate |
|---|---|---|---|---|
| 1 | y1/m1/d1 h1:m1 | C1 | ESBP1 | SBP1,DBP1,PLS1 |
| 2 | y2/m2/d2 h2:m2 | C1 | ESBP2 | SBP2,DBP2,PLS2 |
| 3 | y3/m3/d3 h3:m3 | C2 | ESBP3 | SBP3,DBP3,PLS3 |
| . | . | . | . | . |
| . | . | . | . | . |
| . | . | . | . | . |

FIG. 6

| Inflation Time (sec) | Degree of Blood Congestion |
|---|---|
| $\leq 20$ | C1 |
| 21~30 | C2 |
| 30~40 | C3 |
| 40~50 | C4 |
| 50~60 | C5 |

No Blood Congestion

With Blood Congestion

BLOOD PRESSURE MEASUREMENT DEVICE

BACKGROUND OF THE INVENTION

1. Field of the Invention

The present invention relates to a blood pressure measurement device, and more particularly to a blood pressure measurement device that measures blood pressure taking into account congestion occurred at a peripheral side of the measurement location.

2. Description of the Related Art

Blood pressure is one indicator for analyzing circulatory diseases and is effective at preventing diseases of the cardiovascular system such as strokes, heart failure, heart attacks, and the like by performing risk analysis based on blood pressure.

Recent research indicates that blood pressure measured at home (home blood pressure) is more useful in the diagnosis of circulatory diseases than blood pressure measured by a health care facility (casual blood pressure). In conjunction with this, electronic sphygmomanometers that can be used at home are growing in popularity.

Oscillometric methods and microphone methods are mainly used as measurement principles for electronic sphygmomanometers for home use. With oscillometric methods, a cuff is wrapped around a measurement location such as an upper arm and the pressure inside the cuff (cuff pressure) is quickly increased to a predetermined pressure (for example, systolic blood pressure+30 mmHg) and then the cuff pressure is gradually decreased. Volume change occurring in the artery at that time is detected as a slight pressure fluctuation (pressure pulse wave amplitude) superimposed on the cuff pressure. The cuff pressure detected when the pressure pulse wave amplitude suddenly increases determines the systolic blood pressure, and the cuff pressure detected when the pressure pulse wave amplitude suddenly decreases determines the diastolic blood pressure. Furthermore, blood pressure may also be determined from the detected pressure pulse wave amplitude at the time when the cuff pressure gradually increases. An electronic sphygmomanometer that uses an oscillometric method is represented in, for example, Japanese Unexamined Patent Application No. S62-268532

Meanwhile, with microphone methods, similar to that with the oscillometric method, a cuff is wrapped around a measurement location such as an upper arm, and the cuff pressure is quickly increased to a predetermined pressure (for example, systolic blood pressure+30 mmHg) and then the cuff pressure is gradually decreased. Sounds generated in conjunction with blood flow of an artery as cuff pressure is adjusted by increasing or decreasing pressure, so called Korotkoff sounds, are detected by a microphone embedded within the cuff. Based on the detected result, the cuff pressure detected at the time that the Korotkoff sounds appear determines the systolic blood pressure, and the cuff pressure detected at the time when the Korotkoff sounds weaken or disappear determines the diastolic blood pressure.

SUMMARY OF THE INVENTION

In either of the measurement methods given above, wherein the measurement location is at the upper arm, the cuff is wrapped around the upper arm and as the cuff pressure is increased, veins that have a low internal pressure are obstructed by the cuff pressure that is lower than the diastolic blood pressure (for example, 40 mmHG). However, because the arteries are not obstructed, the blood flow collects at the peripheral side (forearm) of the upper arm. The phenomenon of blood collecting at this peripheral side location is known as "congestion."

As congestion occurs at the peripheral side location, the likelihood of errors in blood pressure measurement accuracy increases. In other words, the difference in artery pressures between the measurement location and the peripheral side location gets smaller due to congestion at the peripheral side location, which results in a reduction in the blood flow amount.

Therefore, with the oscillometric method, because blood pressure is determined by detecting artery volume changes due to blood flow as pressure pulse wave amplitude superimposed on cuff pressure, the artery volume change is smaller as congestion occurs at the peripheral side location and the blood flow amount decreases. As a result, the detected pressure pulse wave amplitude is smaller, and thus, errors may be included in the detected blood pressure value. Further, with the microphone method, because blood pressure is determined by detecting Korotkoff sounds generated within an artery due to blood flow, the Korotkoff sounds become smaller as the blood flow amount is reduced due to the generation of congestion at the peripheral side location. Thus, errors may be included in the detected blood pressure value.

However, because neither the conventional oscillometric method nor the microphone method as given in Patent Document 1 and the like are measurement methods that consider congestion, accurately measuring blood pressure is difficult.

Therefore, one or more embodiments of the present invention provide a blood pressure measurement device that measures blood pressure with high precision.

According to one or more embodiments of the present invention, a blood pressure measurement device comprises: a cuff for wrapping around a measuring location of an arm of a patient; an inflation/deflation control unit that controls inflation and deflation of the cuff; a pressure sensor connected to the cuff for detecting a cuff pressure and pulse waves that are superimposed on the cuff pressure; a CPU stored in the body of the device, the CPU comprising; a blood pressure measurement section that calculates value of blood pressure of the patient based on the cuff pressure and pulse waves detected by the pressure sensor; a blood congestion determination section that determines a degree of blood congestion occurred at a peripheral side of the measurement location due to the cuff pressure on the measurement location in accordance with a predetermined method; and a blood pressure correction section that calculates corrected blood pressure value based on the degree of the blood congestion; and a display that displays the corrected blood pressure value.

According to one or more embodiments of the present invention, a blood pressure measurement device comprises: a cuff for wrapping around a measuring location of an arm of a patient; an inflation/deflation control unit connected to the cuff for controlling inflation and deflation of the cuff; a cuff pressure detecting unit connected to the cuff for detecting a cuff pressure at the measurement location; a microphone connected to the cuff for collecting Korotkoff sounds at the measurement location, a blood pressure measurement unit that measures blood pressure value of the patient based on the Korotkoff sounds collected during the inflation or deflation of the cuff; a blood congestion determination unit that determines a degree of blood congestion occurred at a peripheral side of the measurement location due to the cuff pressure on the measurement location in accordance with a predetermined method; and a threshold value determination unit for setting a threshold value based on the degree of blood congestion; a blood pressure calculation unit that compares voltage value input based on the degree of blood congestion and calculates systolic and diastolic blood pressure value based on the cuff pressure of at the time when the input voltage is found to be over or below the threshold value; and a display that displays the systolic and diastolic blood pressure value calculated by the blood pressure calculation unit.

According to one or more embodiments of the present invention a method of measuring blood pressure comprises: inflating or deflating a cuff that is wrapped around a measurement location of an arm of a patient; detecting a cuff pressure and pulse waves that are superimposed on the cuff pressure; measuring blood pressure of the patient based on the cuff pressure and pulse waves; measuring a degree of blood congestion occurred at a peripheral side of the measurement location due to the cuff pressure on the measurement location in accordance with a predetermined method; correcting the measured blood pressure based on the degree of blood congestion; displaying the corrected blood pressure value of a display.

According to one or more embodiments of the present invention, a method of measuring blood pressure comprises: inflating or deflating a cuff that is wrapped around a measurement location of an arm of a patient; collecting Korotkoff sounds occurred during the inflation or deflation of the cuff; measuring blood pressure of the patient based on collected Korotkoff sounds; determining a degree of blood congestion occurred at a peripheral side of the measurement location due to the cuff pressure on the measurement location in accordance with a predetermined method; correcting the measured blood pressure based on the degree of blood congestion; displaying the corrected blood pressure value of a display.

According to one or more embodiments of the present invention, blood pressure can be measured illuminating the effects of congestion by acquiring a blood pressure using congestion at a peripheral side from the measured location.

BRIEF DESCRIPTION OF THE DRAWINGS

FIG. 4 is a diagram to explain measurement data stored in memory according to an embodiment the present invention.

FIG. 6 is a diagram illustrating a table containing inflation time and degree of blood congestion according to an embodiment of the present invention.

DETAILED DESCRIPTION OF INVENTION

Figure 1:
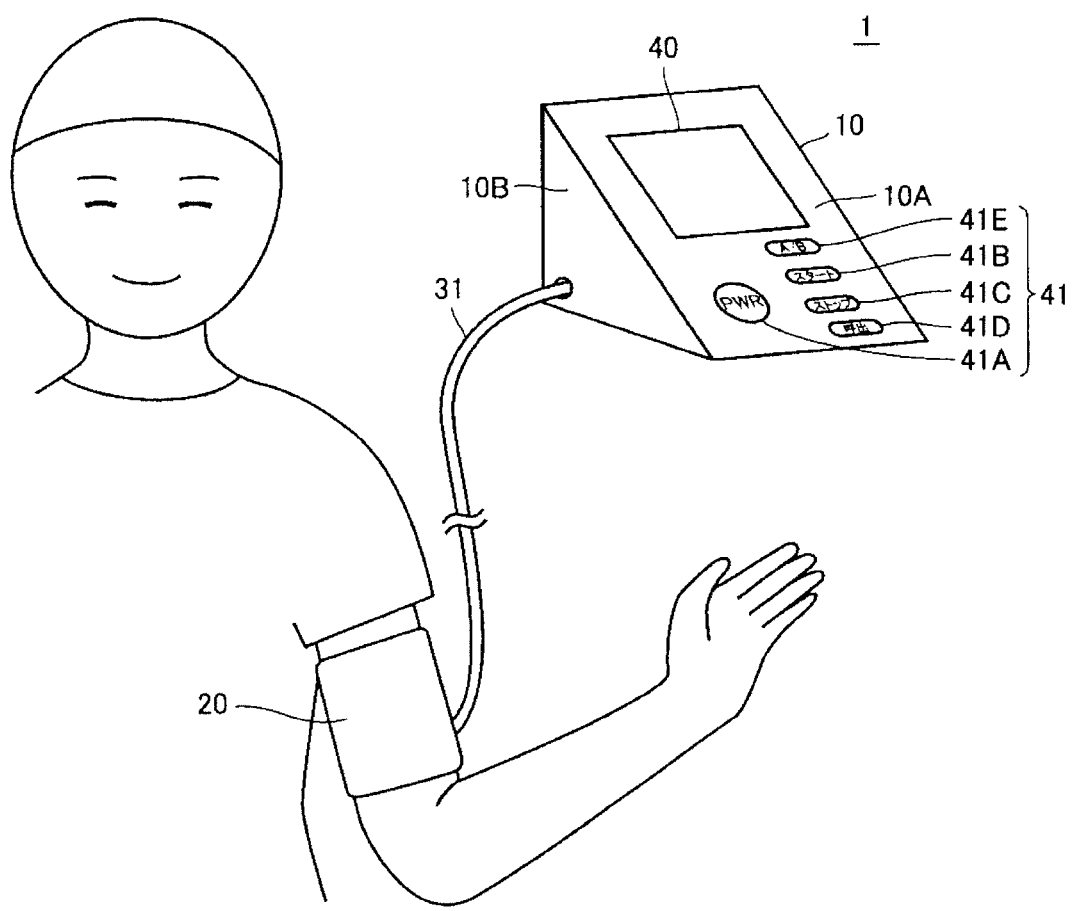
FIG. 1 is an outline perspective view of an electronic sphygmomanometer according to an embodiment of the present invention.

Hereinafter, embodiments of the present invention will be described in detail with reference to drawings. Like elements in the various figures are denoted by like reference numerals for consistency and the description thereof will not be repeated.

The electronic sphygmomanometer according to this embodiment determines parameter values for use in blood pressure calculations of systolic blood pressure and diastolic blood pressure based on "degree of blood congestion," which is the extent of "congestion" described above. Here, a large amount of blood flow collecting at the peripheral side due to congestion will be referred to as high, and a small amount will be referred to as low.

(Appearance and Configuration)

One example of a blood pressure measurement device will be given in an embodiment of the present invention using an electronic sphygmomanometer 1.

FIG. 1 is an outline perspective view of an electronic sphygmomanometer 1 according to an embodiment of the present invention. Referencing FIG. 1, the electronic sphygmomanometer 1 is provided with a main body section 10, a cuff 20 that manually wraps around, for example, an upper arm that is a measurement location of a patient, and an air tube 31 for connecting the main body section 10 to the cuff 20.

The main body section 10 has an installation surface that contacts a platform such as a desk, a top surface 10A made of the installation surface and a predetermined angle, two side surfaces 10B that are perpendicular surfaces to the installation surface, and a back surface (not shown). The air tube 31 is connected to the left side surface 10B of the main body section 10.

The top surface 10A of the main body section 10 is disposed with a display unit 40 for displaying measured results and the like in an operation unit 41 that is operated by a user (represented by a patient) to input instructions. The display unit 40 may be configured by, for example, a display made of liquid crystal or the like. The operation unit 41 includes a power switch 41A that receives an operation for switching the power on and off, a measurement switch 41B and stop switch 41C that receives an operation for instruction input to start and stop measurement, a memory switch 41D, and a user selection switch 41E for receiving an operation that selectively designates a user (patient) of the electronic sphygmomanometer 1. The memory switch 41D is operated to read a previously measured result from memory and to instruct display of the read measured result.

The cuff 20 is a belt shaped bag having a substantial rectangular shape, and an air bladder 21 is built-in within the bag (see FIG. 2 described below). The cuff 20 wraps such that the extended edge in the long direction follows along the circumference of the measurement location (e.g., arm circumference).

Figure 2:
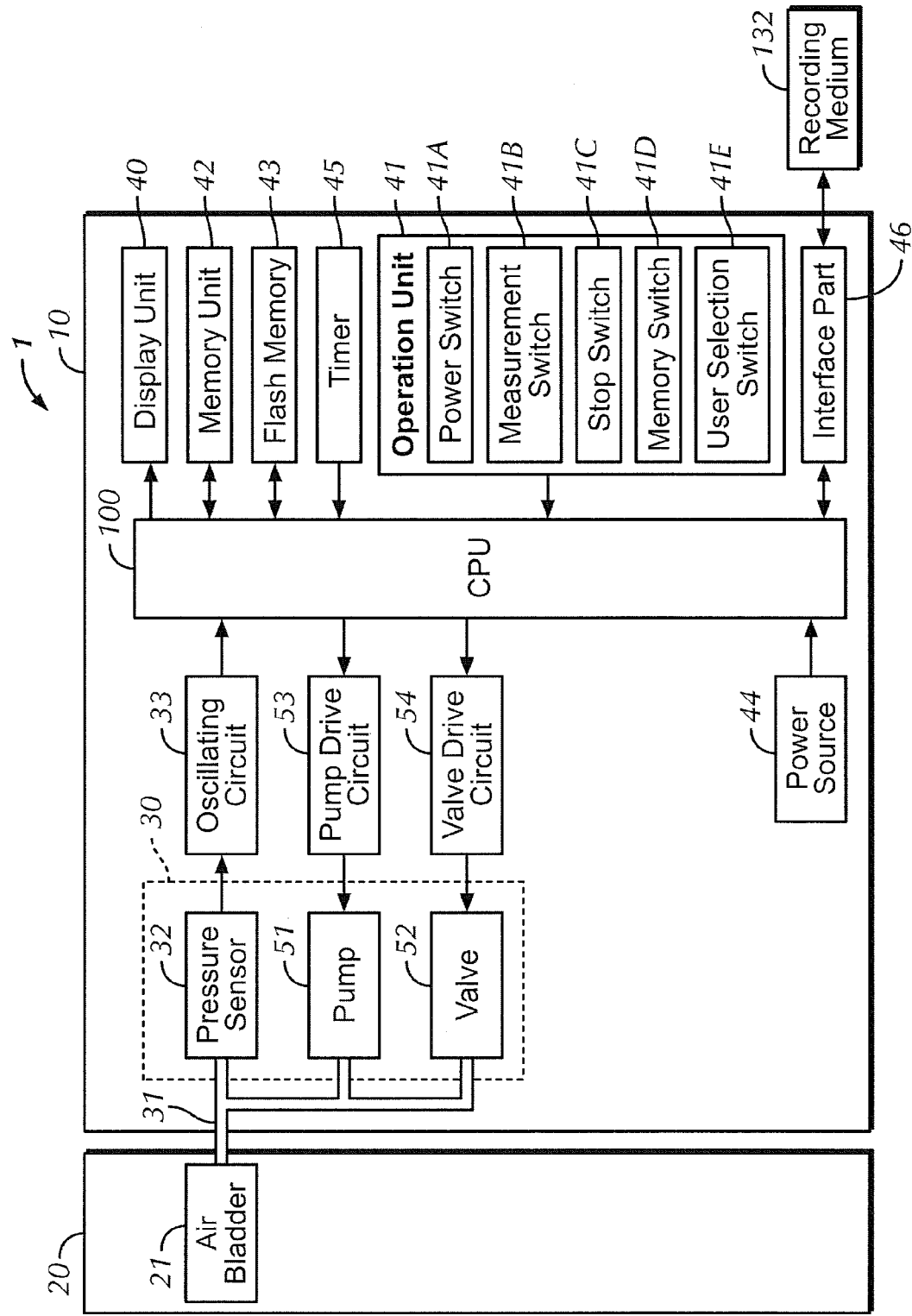
FIG. 2 is a diagram of a hardware configuration of an electronic sphygmomanometer according to an embodiment of the present invention.

FIG. 2 is a block diagram of a hardware configuration of an electronic sphygmomanometer 1 according to an embodiment of the present invention.

Referencing FIG. 2, the air bladder 21 is connected to a system 30 via the air tube 31. The main body section 10 includes a central processing unit (CPU) 100 that centrally controls each part of the air system 30, in addition to the display unit 40, an operation unit 41 that provides all types of arithmetic processing, a memory unit 42 for storing a program and various data to run predetermined operations by the CPU 100, flash memory 43, which is one example of nonvolatile memory, for storing measure blood pressure, power source 44 for supplying power to the CPU 100, a timer 45 for keeping track of time, and an interface part 46 for reading and writing a program and data from a removable storage medium 132.

In this embodiment, the electronic sphygmomanometer 1 is used for a plurality of patients and is thus provided with a user selection switch 41E; however, if not for common use, the user selection switch 41E may be omitted. Further, the measurement switch 41B and the power switch 41A may be used commonly. In such case, the measurement switch 41B may be omitted.

The air system 30 includes a pressure sensor 32 to detect the pressure within the air bladder 21 (hereinafter referred to as cuff pressure), a pump 51 to supply air to the air bladder 21 to increase cuff pressure, and an opening and closing valve 52 to fill and release air for the air bladder 21.

The main body section 10 includes, related to the air system 30, an oscillating sensor 33, a pump drive circuit 53, and a valve drive circuit 54.

The pressure sensor 32 is a capacitance type pressure sensor in which the capacitance value changes depending on the cuff pressure. The oscillating circuit 33 outputs signals of an oscillation frequency that corresponds to the capacitance value of the pressure sensor 32 (hereinafter referred to as pressure signal) to the CPU 100. The CPU 100 detects pressure by converting the signals obtained from the oscillating signal 33 to pressure. The pump drive circuit 53 controls the pump 51 based on control signals given from the CPU 100. The valve drive circuit 54 controls the opening and closing of the valve 52 based on control signals given from the CPU 100.

Note that although the air bladder 21 is included in the cuff 20, the fluid supplied to the cuff 20 is not limited to air and may be, for example, a liquid or gel. Or, it is not limited to a fluid, but may also be a uniform fine particle such as microbeads.

(Function Configuration)

Figure 3:
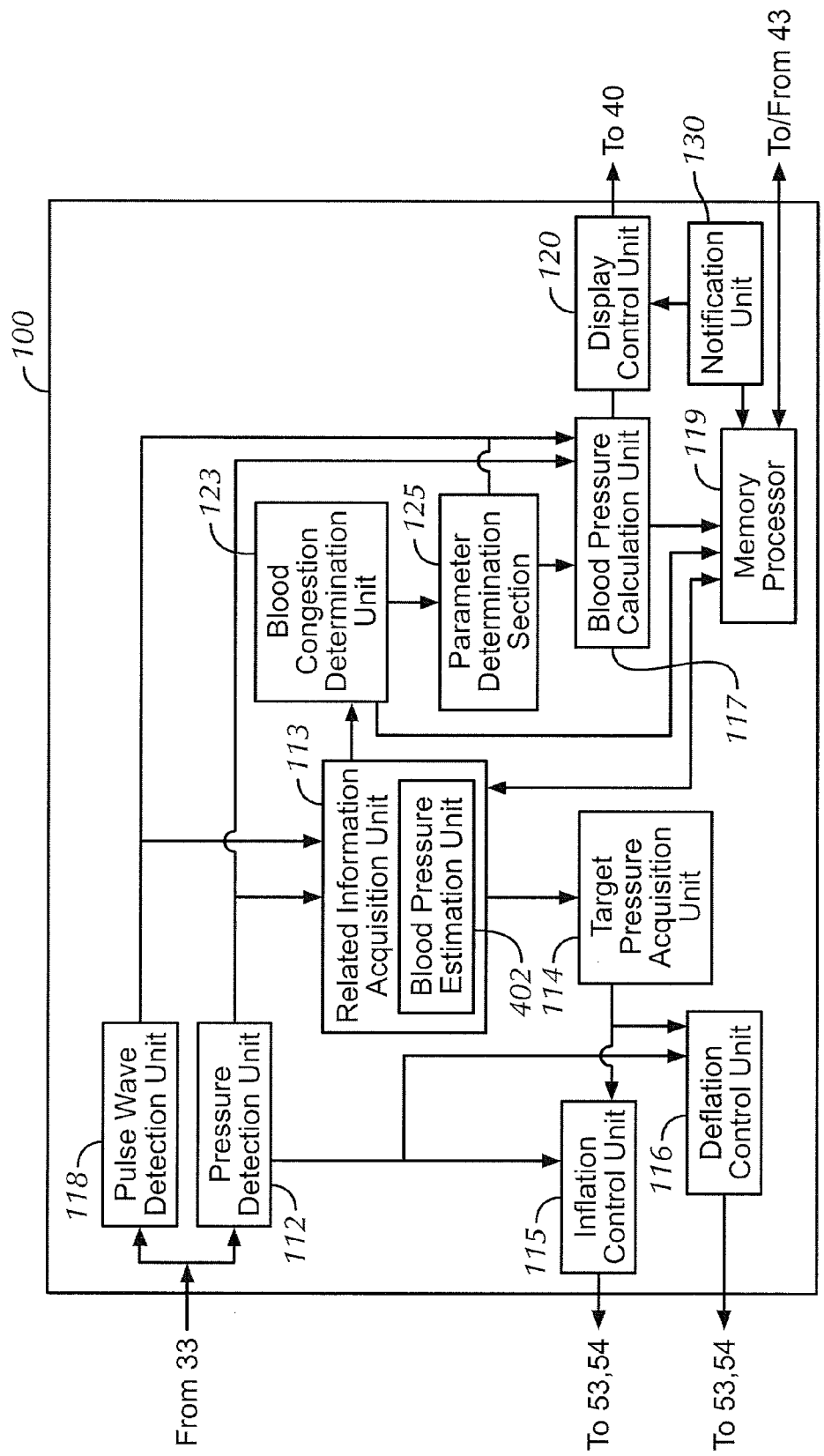
FIG. 3 is a functional configuration diagram of an electronic sphygmomanometer according to an embodiment of the present invention.

FIG. 3 is a function block diagram illustrating a function configuration of the electronic sphygmomanometer 1 according to an embodiment of the present invention. Referencing FIG. 3, the CPU 100 is provided with a pulse wave detection unit 118 and a pressure detection unit 112 that inputs the output signal from the oscillating circuit 33, a related information acquisition unit 113 that includes a blood pressure estimation unit 402, a target pressure acquisition unit 114, a blood congestion determination unit 123 that determines the degree of blood congestion, a parameter determination section 125 for variably determining a value of a parameter for calculating blood pressure (systolic blood pressure and diastolic blood pressure) based on the degree of blood congestion, an inflation control unit 115 and deflation control unit 116 that outputs control signals to the pump drive circuit 53 and the valve drive circuit 54, a blood pressure calculation unit 117 for calculating a blood pressure value according to a predetermined operation using a parameter according to an oscillometric method, a memory processor 119 for reading and writing (accessing) data of flash memory 43, a display control unit 120 to control display of the display unit 40, and a notification unit 130 for outputting guidance based on the degree of blood congestion determined at a time of a previous blood pressure measurement.

The inflation control unit 115 and the deflation control unit 116 send control signals to the pump drive circuit 53 and the valve drive circuit 54 to regulate cuff pressure. Specifically, the inflation control unit 115 and the deflation control unit 116 output control signals to inflate cuff pressure and to deflate cuff pressure. In this embodiment, a blood pressure derivation process is performed by the blood pressure calculation unit 117 during the process of decompressing cuff pressure at a constant rate. The pulse wave detection unit 118 detects a pulse wave signal superimposed on a pressure signal from the oscillating circuit 33. The pressure detection unit 112 converts the pressure signal from the oscillating circuit 33 to a pressure value and outputs.

The target pressure acquisition unit 114 acquires a target pressure value for the time of blood pressure measurement using a blood pressure estimated by the blood pressure estimation unit 402.

Here, a measurement section is configured to include the timer 45, cuff 20, pressure regulator, and pressure detection unit 112 described above. The pressure regulator includes the inflation control unit 115 and the deflation control unit 116 for regulating by increasing or decreasing cuff pressure.

The blood pressure calculation unit 117 calculates a blood pressure value using a parameter based on cuff pressure detected by the pressure detection unit 112 during a process where the cuff pressure is regulated by the pressure regulator. More specifically, blood pressure (systolic blood pressure and diastolic blood pressure) as well as pulse rate are calculated using the parameter and pulse wave signals input from the pulse wave detection unit 118 and the pressure value from the pressure detection unit 112. The pulse rate is calculated according to a known procedure using a pulse rate signal and therefore a detailed description thereof is omitted.

The related information acquisition unit 113 acquires information related to the blood pressure measurement based on information output from the measurement section. The blood congestion determination unit 123 determines the degree of blood congestion at a peripheral side of the measurement location using the acquired related information.

(Example of Storing Measurement Data)

FIG. 4 is a diagram to explain measurement data stored in memory according to an embodiment the present invention. Measurement data that includes a blood pressure value is stored in table 431 of flash memory 43, and each section of the electronic sphygmomanometer 1 accesses (reads and writes) data of the table 431 via the memory processor 119.

Measurement time and date 421, degree of blood congestion 422, estimated systolic blood pressure 423, and blood pressure value/pulse rate 427 are associated with ID data that identifies the patient and is stored in the table 431.

The ID data indicates an identifier according to an operation of the user selection switch 41E. The measurement time and date 421 indicates a blood pressure measurement time, and more typically indicates the date and time based on time data received from the timer 45 at the time of completing blood pressure measurement. The degree of blood congestion 422 indicates the degree of blood congestion C (such as C1, C2, and the like) determined by the blood congestion determination unit 123. The estimated systolic blood pressure 423 indicates systolic blood pressure estimated by the blood pressure estimation unit 402 (estimated systolic blood pressure ESBP) based on pressure signals after starting blood pressure measurement. The blood pressure value/pulse rate 427 indicates a blood pressure value acquired by the blood pressure calculation unit 117 (systolic blood pressure SBP and diastolic blood pressure DBP) and a pulse rate PLS at the time of blood pressure measurement.

Here, although each of the data is associated by storing these data points in a table format, as long as an association can be identified in the flash memory 43, the storage format is not limited to a table.

(Determining Degree of Blood Congestion)

The degree of blood congestion is calculated (determined) using information related to the blood pressure measurement. In this embodiment, different types of blood congestion can be calculated by differentiating information related to blood pressure measurement used in the calculation of the degree of blood congestion. First, an explanation will be given of determining the degree of blood congestion using inflation time as information related to blood pressure measurement.

<Determination According to Inflation Time>

Figure 5:
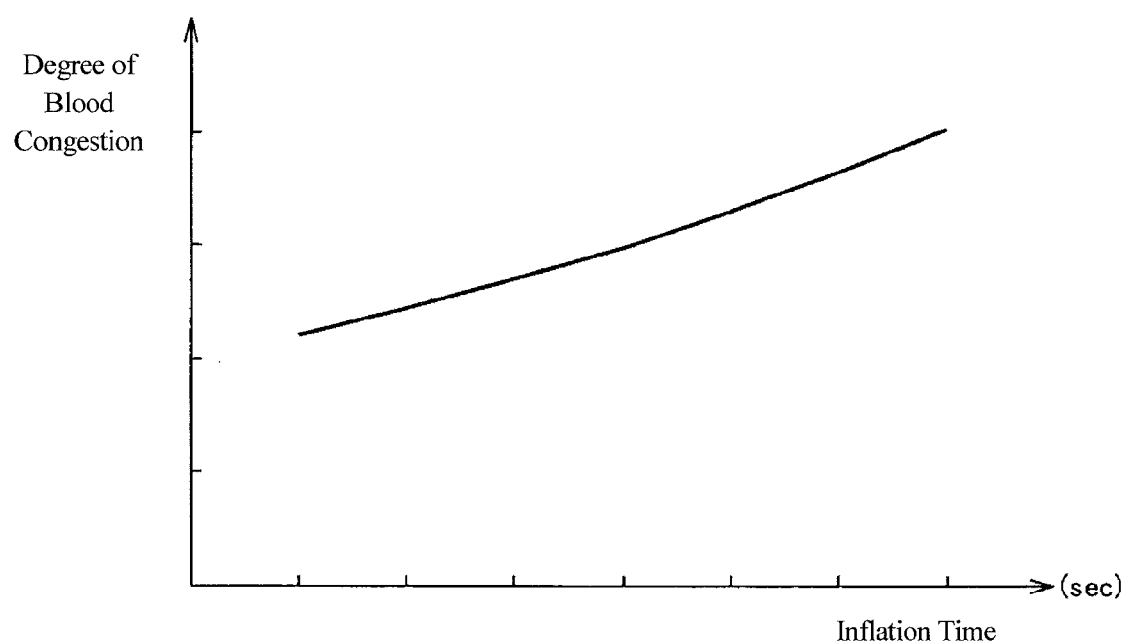
FIG. 5 is a graph illustrating a relationship between a degree of blood congestion and inflation time according to an embodiment of the present invention.

An explanation will be given for determining a degree of blood congestion with reference to FIGS. 5 and 6. In FIG. 5, the relationship between the degree of blood congestion and inflation time, which is the elapsed time from the start of increasing pressure, is illustrated by a graph in this embodiment. The vertical axis of the graph indicates the degree of blood congestion, and the horizontal axis indicates inflation time (unit: sec), and the graph indicates the experimental results of the inventors. According to the graph, when increasing pressure at a constant rate, the degree of blood congestion increases as inflation time increases.

The graph of FIG. 5 can be replaced by the following equation (1). The blood congestion determination unit 123 determines the degree of blood congestion by calculating congestion C according to equation (1).

$$C = \alpha \times t^2 + \beta \times t + \gamma \qquad \text{Equation (1)}$$

Variables in equation (1) are as follows: C indicates the degree of blood congestion, t indicates inflation time, $\alpha$, $\beta$, and $\gamma$ indicate constants found by experiment in advance.

In FIG. 6, table 441 shows the stored inflation time and congestion C associations illustrated by the graph of FIG. 5. Table 441 is stored in advance in flash memory 43. The degree of blood congestion may be determined by searching table 441 as an alternative to equation (1). Specifically, the blood congestion determination unit 123 reads the degree of blood congestion C that corresponds to the inflation time by searching table 441 based on the inflation time indicated by time data from the timer 45. The degree of blood congestion is determined accordingly.

(Determining Parameter Values for Blood Pressure Calculation)

In this embodiment, the parameter determination section 125 determines the parameter values according to the oscillometric method using a degree of blood congestion determined by the blood congestion determination unit 123.

First, blood pressure according to the oscillometric method is calculated by the blood pressure calculation unit 117. This process is explained in reference to FIG. 7. The graph of FIG. 7 is disclosed in Patent Document 1 described above and is taken by cuff pressure (unit: mmHg) detected according to the pressure detection unit 112 for the horizontal axis and the pulse wave amplitude value (unit: mmHg) detected by the pulse wave detection unit 118 during the process of deflation for the vertical axis.

Figure 7:
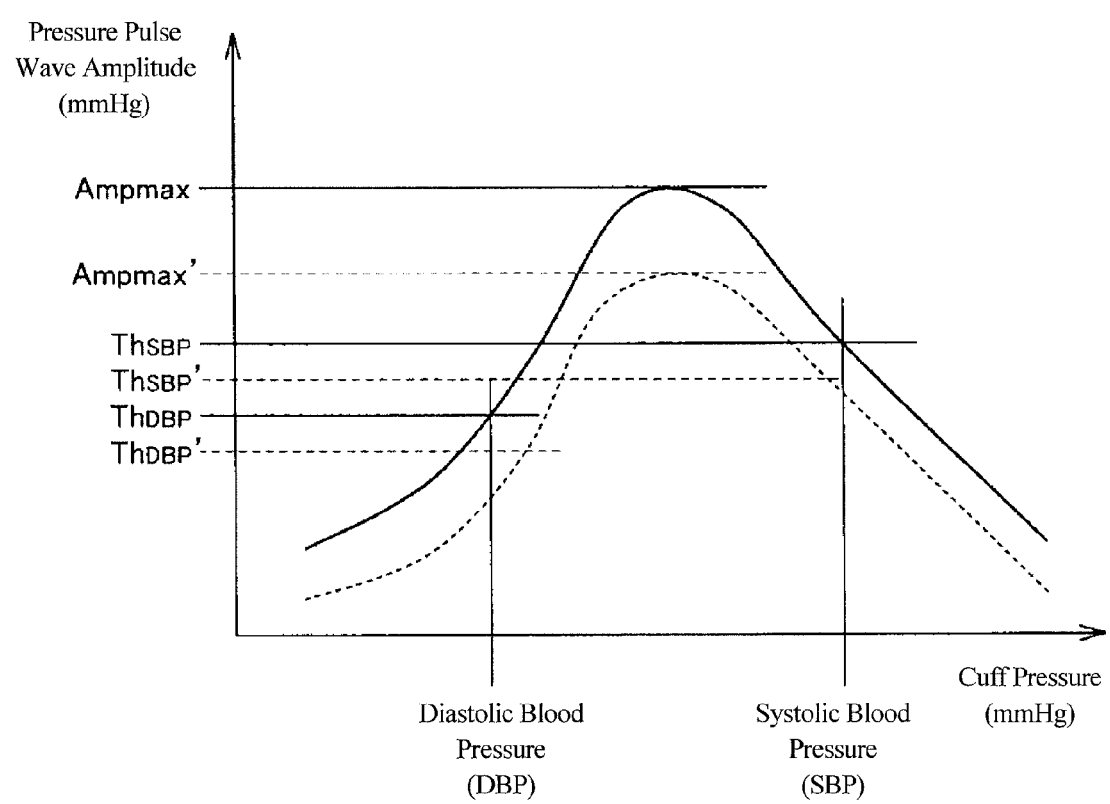
FIG. 7 is a graph illustrating a relationship between pressure pulse wave amplitude value and cuff pressure according to an embodiment of the present invention.

Plotting pressure pulse wave amplitude values detected in conjunction with changes in cuff pressure is referred to as an envelope curve, and two envelope curves are expressed in FIG. 7 shown by a solid line and a broken line according to experiments by the inventors. The envelope curve illustrated by the solid line indicates where congestion did not occur at a peripheral side, and the envelope curve illustrated by the broken line indicates where congestion occurred.

Here, when looking at the envelope curve of the solid line in FIG. 7, the parameter determination section 125 multiplies the maximum amplitude value Ampmax of the pulse wave amplitude by a predetermined ratio and then adds a predetermined offset value, and this calculated value is determined to be the parameter value. The parameter ThSBP used for calculating systolic blood pressure and the parameter ThDBP used for calculating diastolic blood pressure can be calculated according to the following equations (2) and (3), respectively.

$$Th\text{SBP} = \text{Ampmax} \times a\text{SBP} + b\text{SBP} \qquad \text{equation (2)}$$

$$Th\text{DBP} = \text{Ampmax} \times a\text{DBP} + b\text{DBP} \qquad \text{equation (3)}$$

The variables given above are values that were determined by prior testing and the like, and aSBP and aDBP indicate predetermined ratios, while bSBP and bDBP indicate predetermined offset values.

The blood pressure calculation unit 117 synchronizes and inputs the pressure pulse wave input from the pulse wave detection unit 118 at the time of measurement with cuff pressure input from the pressure detection unit 112, and stores each of these input data into flash memory 43 according to a time series based on time data of the timer 45. By this, the data stored in the flash memory 43 is indicated in the envelope curve. Further, the values for the parameters ThSBP and ThDBP calculated by equations (2) and (3) from the parameter determination section 125 are input. Further, the blood pressure calculation unit 117 extracts the cuff pressure that corresponds to the intersecting point for the input parameter value and the envelope curve of the solid line in FIG. 7 according to the data in flash memory 43, and the systolic blood pressure (SBP) at the high pressure side and the diastolic blood pressure (DBP) at the low pressure side are, respectively, determined from among the extracted cuff pressures.

Meanwhile, if congestion occurs at the peripheral side, the values for the parameters ThSBP and ThDBP calculated by equations (2) and (3) cannot be used. In other words, the pressure pulse wave amplitude detected by the pulse wave detection unit 118 is smaller, and as a result, the envelope curve acquired by the blood pressure calculation unit 117 becomes that illustrated by the broken line in FIG. 7.

Here, if the envelope curve of the broken line has the same shape as the envelope curve of the solid line, and was merely smaller in its overall shape, the values of the parameters ThSBP and ThDBP could be utilized as is without the need to recalculate the parameter values.

However, when adopting a method that measures blood pressure during deflation, the measured blood pressure becomes more susceptible to congestion as cuff pressure becomes lower. In other words, when comparing pressure pulse wave amplitude at the time of systolic blood pressure to pressure pulse wave amplitude at the time of diastolic blood pressure, the pressure pulse wave amplitude at the time of diastolic blood pressure is more susceptible to congestion making the pressure pulse wave amplitude even smaller. Therefore, using the parameter value calculated by the envelope curve of the solid line, as is in the envelope curve illustrated by the broken line, brings about errors due to congestion in the calculated blood pressure. Therefore, in order to remove the errors and calculate an accurate blood pressure, the parameter determination section 125 calculates the values of parameters ThSBP and ThDBP using the degree of blood congestion. Parameters ThSBP and ThDBP are corrected using, for example, equations (4) and (5).

$$ThSBP = Ampmax \times aSBP \times CSBP + bSBP \quad \text{equation (4)}$$

$$ThDBP = Ampmax \times aDBP \times CDBP + bDBP \quad \text{equation (5)}$$

Here, the values of variables CSBP and CDBP are values calculated based on the degree of blood congestion calculated in equation (1), and are values determined by testing in advance.

Further, with equations (5) and (4) described above, the variables aSBP and aDBP of equations (2) and (3) are corrected by the degree of blood congestion, but may also be used to correct variables bSBP and bDBP by the degree of blood congestion, or may be used to correct both.

In this way, even if congestion occurs (envelope curve of the broken line of FIG. 7), values for parameters ThSBP and ThDBP can be determined to remove the errors caused by congestion, and therefore, the blood pressure calculation unit 117 can determine systolic blood pressure and diastolic blood pressure similar to when congestion has not occurred (envelope curve of the solid line of FIG. 7).

(Correcting Calculated Blood Pressure Values)

With the above, the values of the parameters for calculating blood pressure are corrected by the degree of blood congestion, but accurate blood pressure, in which errors due to the degree of blood congestion are removed, may be determined by correcting blood pressure based on the degree of blood congestion as a substitute for parameter values.

First, it is assumed that the blood pressure calculation unit 117 acquires data of the envelope curve of the broken line in FIG. 7 using the pressure pulse wave amplitude and the cuff pressure from the pulse wave detection unit 118 and the pressure detection unit 112. The values of parameter ThSBP' used to calculate systolic blood pressure and parameter ThDBP' used to calculate diastolic blood pressure can be calculated by substituting the maximum amplitude value Ampmax from equations (2) and (3) with the maximum amplitude value Ampmax' of the pressure pulse wave amplitude of the envelope curve of the broken line.

If systolic blood pressure and diastolic blood pressure calculated without using parameter values from the parameter determination section 125 are, respectively, represented by the variables SBP' and DBP', an accurate blood pressure can be calculated by the following equations.

$$SBP = SBP' + \text{Offset } CSBP \quad \text{equation (6)}$$

$$DBP = DBP' + \text{Offset } CDBP \quad \text{equation (7)}$$

Here, variables SBP' and DBP' indicate blood pressure values calculated from intersecting points on the envelope curve of the broken line for blood pressure prior to corrections for the degree of blood congestion (provisional blood pressure), which is more correctly stated as the values of the parameters ThSBP' and ThDBP'. The variables Offset CSBP and Offset CDBP are coefficients for correction calculated from the degree of blood congestion calculated by equation (1), and indicate values determined by advance testing.

In this manner, a provisional blood pressure that includes errors due to congestion is calculated and corrections are made on the provisional blood pressure by parameter values based on the degree of blood congestion such that an accurate blood pressure having no errors can be calculated.

In the above, the same type of degree of blood congestion is used regardless of the type of blood pressure being calculated (systolic blood pressure or diastolic blood pressure), but the type of degree of blood pressure used in calculating blood pressure may be differentiated according to the type of blood pressure being calculated. For example, when calculating systolic blood pressure, the degree of blood congestion calculated by the following systolic blood pressure is used, and when calculating diastolic blood pressure, the degree of blood congestion calculated by the following diastolic blood pressure is used, and the like.

(Guidance Output)

In this embodiment, guidance is output based on the degree of blood congestion. Specifically, the notification unit 130 outputs guidance for blood pressure measurement to the patient based on the degree of blood congestion 422 stored in the table 431.

Blood congestion in blood pressure measurement is caused by increasing pressure until the flow of blood in the artery has temporarily stopped due to the cuff 20 being wrapped around a measurement location and continuously measuring blood pressure over a long period of time. Blood congestion is further caused by tightly wrapping the cuff 20 around the measurement location. Therefore, the notification unit 130 outputs guidance at the time of starting blood pressure measurement so as not to generate a blood congestion condition.

First, the notification unit 130 calculates a representative value for a predetermined number for degree of blood congestion 422 stored to the nearest value in the table 431 (average value or center value or the like), and the calculated representative value and the predetermined value are compared and it is determined whether the degree of blood congestion of the representative value is higher based on the comparison result.

If it is determined that the representative value of the degree of blood congestion is higher, and it is determined that there was a short measurement interval, the notification unit 130 issues a warning to increase the measurement interval by indicating on the display unit 40 a message stating, "Risk of blood congestion. Please measure with a sufficient time interval." In other words, a measurement interval is calculated based on the measurement date and time 421 that corresponds to the degree of blood congestion 422 stored in the nearest value of the table 431. If it is determined that the measurement interval is shorter than the predetermined time based on a comparison result by comparing the calculated measure interval and the predetermined time, the message is output.

Note that if the determined result is that the representative value is not high, or that the measurement interval is not shorter than the prescribed time, message output by the notification unit 130 can be omitted.

(Process Flowchart)

Figure 8:
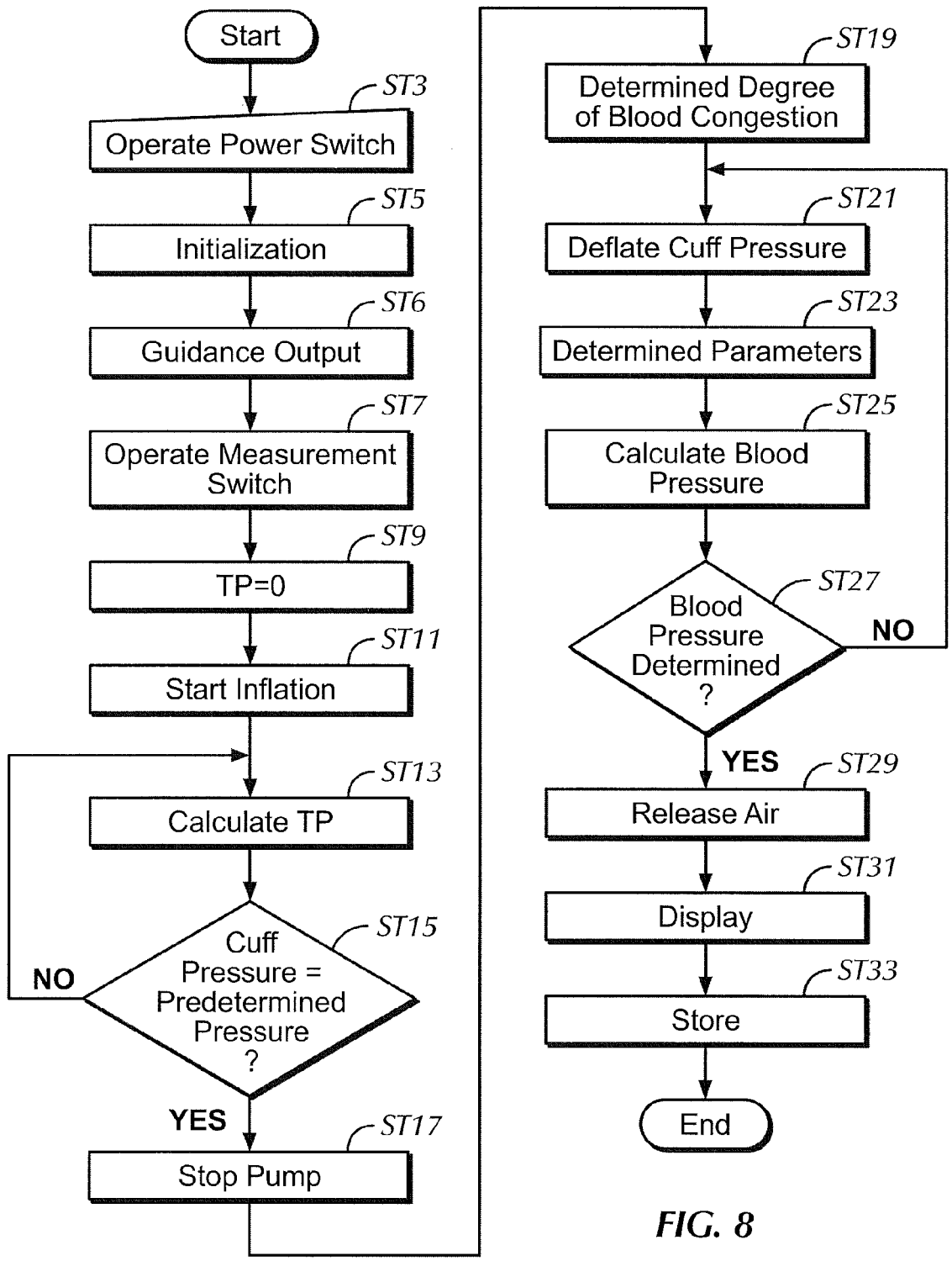
FIG. 8 is a process flowchart according to an embodiment of the present invention.

Next, a measurement operation according to the oscillometric method of an electronic sphygmomanometer 1 will be explained according to the flowchart in FIG. 8. A program according to the flowchart in FIG. 8 is stored in a memory unit 42 in advance. The CPU 100 reads commands of the program from the memory unit 42 and executes a measurement operation by controlling the operations of each section according to these commands.

First, the CPU 100, after receiving an operation of the power switch 41A by patient, supplies power to each section by controlling the power source 44 (step ST (hereinafter simplified as ST) 3). Subsequently, the CPU 100 and initializes a memory area for processing as initialization, inflates air into the cuff 20, and performs a 0 mmHg correction for the pressure sensor 32 (ST 5). It is assumed that the patient already has the cuff 20 wrapped around the measurement location.

After initialization, the notification unit 130 displays a message on the display unit 40 if necessary according to a determination made by following the guidance procedures given above (ST 6). Accordingly, by the patient following the guidance in the message, measurement is stopped and then measurement can be started after allowing a sufficient time to pass.

Thereafter, the CPU 100 receives an operation of the measurement switch 41B by the user to indicate a measurement start (ST 7), and the related information acquisition unit 113 initializes by setting a value, for example, "0" in the timer variable TP to measure the inflation time (ST 9). The time variable TP is stored in internal memory within the CPU 100. After initialization, pressurization is started. Specifically, the pressure regulator closes the valve 52 and inflates the cuff pressure at a constant rate by driving the pump 51 (ST 11).

The related information acquisition unit 113, in the inflation process after beginning inflation, runs a successive operation for adding the values of the timer variable TP using time data from the timer 45 (ST 13). Accordingly, the value of the timer variable TP indicates inflation time for the continuous inflation operation.

The inflation control unit 115 and the deflation control unit 116 input the cuff pressure detected by the pressure detection unit 112 and compare the input cuff pressure to a predetermined pressure (for example, systolic blood pressure+30 mmHg). Based on the comparison result, the inflation operation continues while it is determined that the cuff pressure does not indicate the predetermined pressure (No at ST 15), and when it is indicated (Yes at ST 15), the deflation control unit 116 stops the pump 51 while the valve 52 is in a closed state (ST 17). When the pump 51 stops, the related information acquisition unit 113 stops adding the timer variable TP. The blood congestion determination unit 123 According to the procedure described above, determines the degree of blood congestion at the peripheral side from the inflation time indicated by the timer variable TP (ST 8).

Next, the deflation control unit 116 gradually opens the valve 52 while the pump 51 is in a stopped state and begins deflation of the cuff pressure (ST 21). From hereafter, the description will transition to the deflation process.

In the deflation process, the parameter determination section 125 follows the procedure described above to determine the parameter values based on the degree of blood congestion (ST 23). Note that, the timing for determining the parameter value based on the degree of blood congestion may be after the degree of blood congestion is determined and is not limited to after transitioning to the deflation process.

The pulse wave detection unit 118 detects the pressure pulse wave amplitude based on volume change of the artery superimposed on the cuff pressure. The blood pressure calculation unit 117 uses the parameter values determined by the parameter determination section 125 and the pressure pulse wave amplitude to calculate blood pressure according to the oscillometric method (ST 25). Further, the pulse rate is also calculated.

According to the CPU 100, it is determined whether both the systolic blood pressure and the diastolic blood pressure are calculated as the blood pressure by the blood pressure calculation unit 117 (ST 27). If it is determined that it has not been calculated (No at ST 27), the process moves to ST 21 and deflation continues, but if it is determined that calculations for both blood pressures have completed, (Yes at ST 27), the deflation control unit 116 fully opens the valve 52 to rapidly release the air within the cuff (ST 29). Further, the calculated blood pressure is displayed in the display unit 40 according to the display control unit 120 (ST 31). In addition, the memory processor 119 stores the calculated blood pressure values and pulse rate 427, the measured date and time 421 based on the time data of the timer 45, and the degree of blood congestion 422 determined by the blood congestion determination unit 123 and associates these in the table 431 (ST 33). Thereafter, the CPU 100 ends the measurement process by turning off the power source 44.

(Another Method for Determining Degree of Blood Congestion)

The method for determining the degree of blood congestion according to this embodiment is not limited to the inflation time described above, but other methods such as that described hereinafter, may also be applied.

<Determination According to Maximum Inflation Value>

Here, a value of a predetermined pressure for ST 15 of FIG. 6 is referred to as a maximum inflation value, and the maximum inflation value is assumed to be stored in the flash memory 43 in advance. The blood congestion determination unit 123 uses the maximum inflation value read from flash memory 43 to determine the degree of blood congestion by a similar procedure to inflation time described above. In other words, if the inflation speed according to the pump 51 is constant, the inflation time described above may be substituted by a maximum inflation value.

The inventors have discovered that the degree of blood congestion can be calculated from the maximum inflation value according to equation (8), and that equation (8) expresses the relationship between maximum inflation value and degree of blood congestion. According to experiments, the degree of blood congestion and the maximum inflation value have a relationship, similar to inflation time, where the degree of blood congestion increases to the extent that the maximum inflation value is high.

$$C = \delta \times Pcmax2 + \epsilon \times Pcmax + \phi \qquad \text{equation (8)}$$

The variables in the equation (8) are as follows: C is the degree of blood congestion, Pcmax is the maximum inflation value, and $\delta$, $\epsilon$, and $\phi$ are constants found by experiment in advance.

Note that the blood congestion determination unit 123 may determine the degree of blood congestion by searching a table in place of equation (8). In other words, maximum inflation values obtained by experimentation and their corresponding degree of blood congestion may be registered in a table in advance, and this table may be stored in flash memory 43. The blood congestion determination unit 123 searches the table based on the maximum inflation value and determines the degree of blood congestion by reading the corresponding degrees of blood congestion.

<Determination According to Inflation Speed>

The blood congestion determination unit 123 may also determine the degree of blood congestion according to inflation speed. In other words, the inflation time until achieving a maximum inflation value is primarily determined according to the inflation speed. Therefore, substituting inflation time and maximum inflation value described above with inflation speed is essentially the same thing.

Here, the inflation speed v is determined by the drive voltage value applied to the pump 51. The blood congestion determination unit 123 inputs the drive voltage value detected by the voltage sensor (not shown) equipped at the input stage of the pump 51 and converts the input voltage value to an inflation speed v according to a predetermined conversion method.

The inventors have discovered that the degree of blood congestion can be calculated from the inflation speed according to equation (9), and that equation (9) expresses the relationship between inflation speed v and the degree of blood congestion. According to equation (9), a relationship is achieved in which the degree of blood congestion increases as inflation speed slows.

$$C=\eta \times v2+\tau \times v+\kappa \qquad \text{equation (9)}$$

The variables in the equation (9) are as follows: C is the degree of blood congestion, v is the inflation speed, and $\eta$, $\tau$, and $\kappa$ are constants found by experiment in advance.

Note that the blood congestion determination unit 123 may acquire the degree of blood congestion by searching a table in place of equation (9). In other words, inflation speed obtained by experimentation and the corresponding degree of blood congestion may be registered in a table in advance, and this table may be stored in flash memory 43. In addition, the blood congestion determination unit 123 searches the table based on the inflation speed and determines the degree of blood congestion by reading the corresponding degrees of blood congestion.

<Determining According to Cuff Size and Measurement Location Circumference Length>

Inflation time and inflation speed described above change depending on the cuff size (size of a capacity for the cuff 20) which can also be stated as the circumferential length of the measurement occasion, and the drive voltage value of the pump 51.

An appropriate size is determined for the cuff size by the measurement location circumference length, and as the measurement location circumference length increases, the cuff size must also increase. For example, when the pump 51 drive set a constant voltage value, the required time until achieving the same cuff pressure is longer as the cuff size increases, and as a result, the degree of blood congestion is higher.

Therefore, in this embodiment, the CPU 100 has an information receiving section that is a function to receive a cuff size or a measurement location circumference length input by a patient by operating the operation unit 41 in advance. The blood congestion determination unit 123 calculates the degree of blood congestion from a predetermined operation using the cuff size or the measurement location circumference length received by the information receiving section.

The blood congestion determination unit 123 may also determine the degree of blood congestion by searching a table in place of the operation. In other words, the cuff size obtained by experimentation and their corresponding degree of blood congestion may be registered in a table in advance, and this table may be stored in flash memory 43. In addition, the blood congestion determination unit 123 searches the table based on the received cuff size and determines the degree of blood congestion by reading the corresponding degrees of blood congestion. Similarly, for the measurement location circumference length, a table in which the measurement location circumference length and its corresponding degrees of blood congestion are recorded is stored in flash memory 43, and corresponding degrees of blood congestion can be read by searching this based on the measurement location circumference length.

Note that the same can be said for a low drive voltage of the pump 51 for the same cuff size or measurement location circumference length. Thus, the degree of blood congestion may also be calculated by the drive voltage of the pump 51, and the corresponding degree of blood congestion may be read using a table.

<Determination According Systolic Blood Pressure>

The blood congestion determination unit 123 may also be configured to determine the degree of blood congestion from the systolic blood pressure of the patient. Specifically, the maximum inflation value described above is a predetermined pressure, for example, systolic blood pressure+30 mmHg. Therefore, replacing the maximum inflation value described above with the systolic blood pressure enables the degree of blood congestion to be determined using a similar procedure.

The inventors have discovered that the degree of blood congestion can be calculated from the systolic blood pressure according to equation (10), and that equation (10) expresses the relationship between systolic blood pressure and the degree of blood congestion. According to the experiments, it has been discovered that the degree of blood congestion increases as systolic blood pressure increases in a similar manner as with the maximum inflation value.

$$C=\mu \times SBP2+v \times SBP+o \qquad \text{equation (10)}$$

The variables in the equation (10) are as follows: C is the degree of blood congestion, SBP is the systolic blood pressure, and $\mu$, $v$, and $o$ are constants found by experiment in advance.

Note that the blood congestion determination unit 123 may acquire the degree of blood congestion by searching a table in place of equation (10). In other words, the systolic blood pressure obtained by experimentation and the corresponding degree of blood congestion may be registered in a table in advance, and this table may be stored in flash memory 43. In addition, the blood congestion determination unit 123 searches the table based on the maximum inflation value and determines the degree of blood congestion by reading the corresponding degrees of blood congestion.

Therefore, the systolic blood pressure used in determining the degree of blood congestion may use a systolic blood pressure estimated using pressure pulse wave amplitude detected in the inflation process by the blood pressure estimation unit 402 (hereinafter referred to as estimated systolic blood pressure).

The blood pressure estimation unit 402 estimates the systolic blood pressure based on output from the pulse wave detection unit 118. Specifically, the pulse wave detection unit 118 extracts and outputs pulse wave signals, which are vibrational components superimposed on cuff pressure. The pulse wave detection unit 118 has a high pass filter function and extracts and outputs pulse waves from cuff pressure using this high pass filter function.

The blood pressure estimation unit 402 inputs pulse wave signals from the pulse wave detection unit 118, detects the start point and end point for each pulse wave of the input pulse wave signals for each beat, and calculates a pressure pulse wave amplitude. Further, of the pulse wave signals input by the inflation process, the pressure pulse wave amplitude identifies the pulse wave having maximum amplitude, and calculates the systolic blood pressure from the predetermined operation using that amplitude value. The estimated systolic blood pressure is acquired accordingly. Therefore, at the time of blood pressure measurement, a configuration may be provided where the target pressure acquisition unit 114 inputs the estimated systolic pressure from the blood pressure estimation unit 402 in the inflation process, calculates the maximum inflation value, which is the target pressure according to the operation of (estimated systolic blood pressure+30 mmHg), and provides the measured value to the regulator as the predetermined pressure for step ST 15. Note that the estimated systolic blood pressure is associated with other measurement data and stored in the table 431 in step ST 33.

Further, the systolic blood pressure used in determining the degree of blood congestion may also be a preliminary systolic blood pressure calculated by using blood pressure calculation parameters prior to correction according to the extent of congestion from the pressure pulse wave amplitude detected during deflation.

Further, although correction is performed by systolic blood pressure, correction may also be performed by pulse pressure (the difference between systolic blood pressure and diastolic blood pressure). In other words, because the oscillometric method calculates blood pressure by change in pressure pulse wave amplitude when cuff pressure is changed, correction by pulse pressure is effective for correcting systolic blood pressure and is especially effective for correcting diastolic blood pressure. In other words, in a method that calculates blood pressure at the time of deflation, it takes a comparatively long time for diastolic blood pressure to be determined after starting deflation for people who have a large pulse pressure. That is, people who have a large difference between their systolic blood pressure and diastolic blood pressure, which increases the degree of blood congestion, experience increases in errors in diastolic blood pressure.

Correction by pulse pressure may use pulse pressure in place of systolic blood pressure SBP of equation (10). Further, degree of blood congestion used in pulse pressure calculation may be a representative value of the degree of blood pressure congestion calculated using at least two or more of the elements from among inflation time, inflation speed, systolic blood pressure, and the like. Specifically, an average value may be used for degree of blood pressure congestion calculated using at least two or more of the elements of inflation time, inflation speed, systolic blood pressure, and the like.

Alternative Embodiment

The blood pressure acquisition unit of this embodiment is a second blood pressure acquisition unit according to a microphone method to be explained hereinafter and is separate from the first blood pressure acquisition unit according to the oscillometric method described above.

Figure 9:
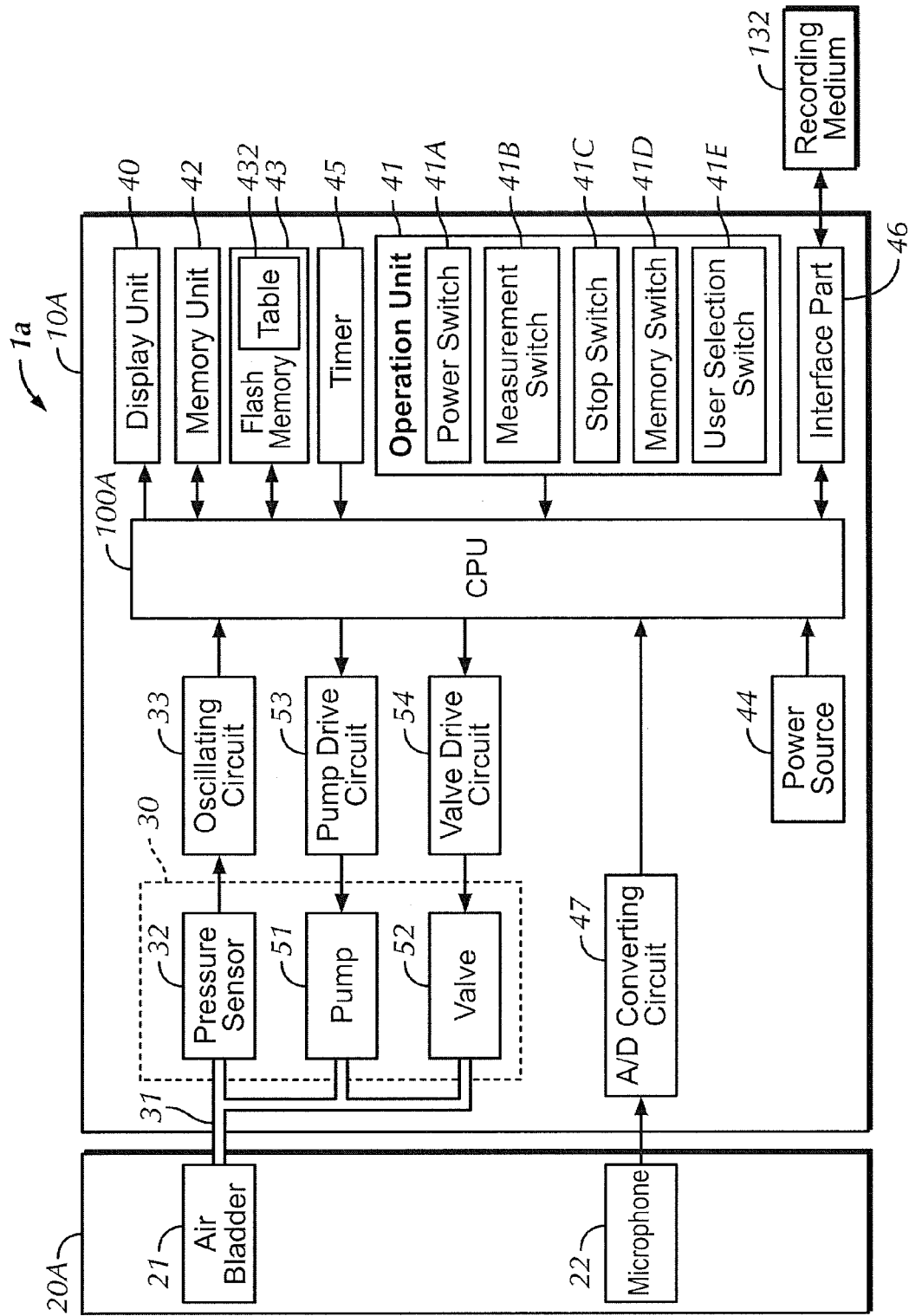
FIG. 9 is a diagram of a hardware configuration of an electronic sphygmomanometer according to another embodiment of the present invention.

The outer appearance of an electronic sphygmomanometer 1A provided with the second blood pressure acquisition unit according to this embodiment is similar to that of FIG. 1. In FIG. 9, a hardware configuration is illustrated for an electronic sphygmomanometer 1A according to another embodiment. Referencing FIG. 9, difference between the configuration of the electronic sphygmomanometer 1 of FIG. 2 is that the electronic sphygmomanometer 1A of FIG. 9 is provided with a main body section 10A instead of the main body section 10 and a cuff 20A instead of the cuff 20. The cuff 20A includes an air bladder 21 and a microphone 22, which is a sound detection unit detects and collects Korotkoff sounds. The main body section 10A is provided with an A/D (analog/digital) converting circuit 47 in addition to the configuration of the main body section 10, and is provided with a CPU 100A in place of the CPU 100. Another configuration of the electronic sphygmomanometer 1A is similar to that illustrated in FIG. 2, and therefore an explanation thereof will be omitted.

The A/D converting circuit 47 converts an output voltage signal from the microphone 22 to digital data and outputs to the CPU 100A. This output voltage indicates the sound pressure level (unit: dB) of the Korotkoff sounds. The larger the sound pressure, the more is recognized as a loud sound.

(Functional Configuration)

Figure 10:
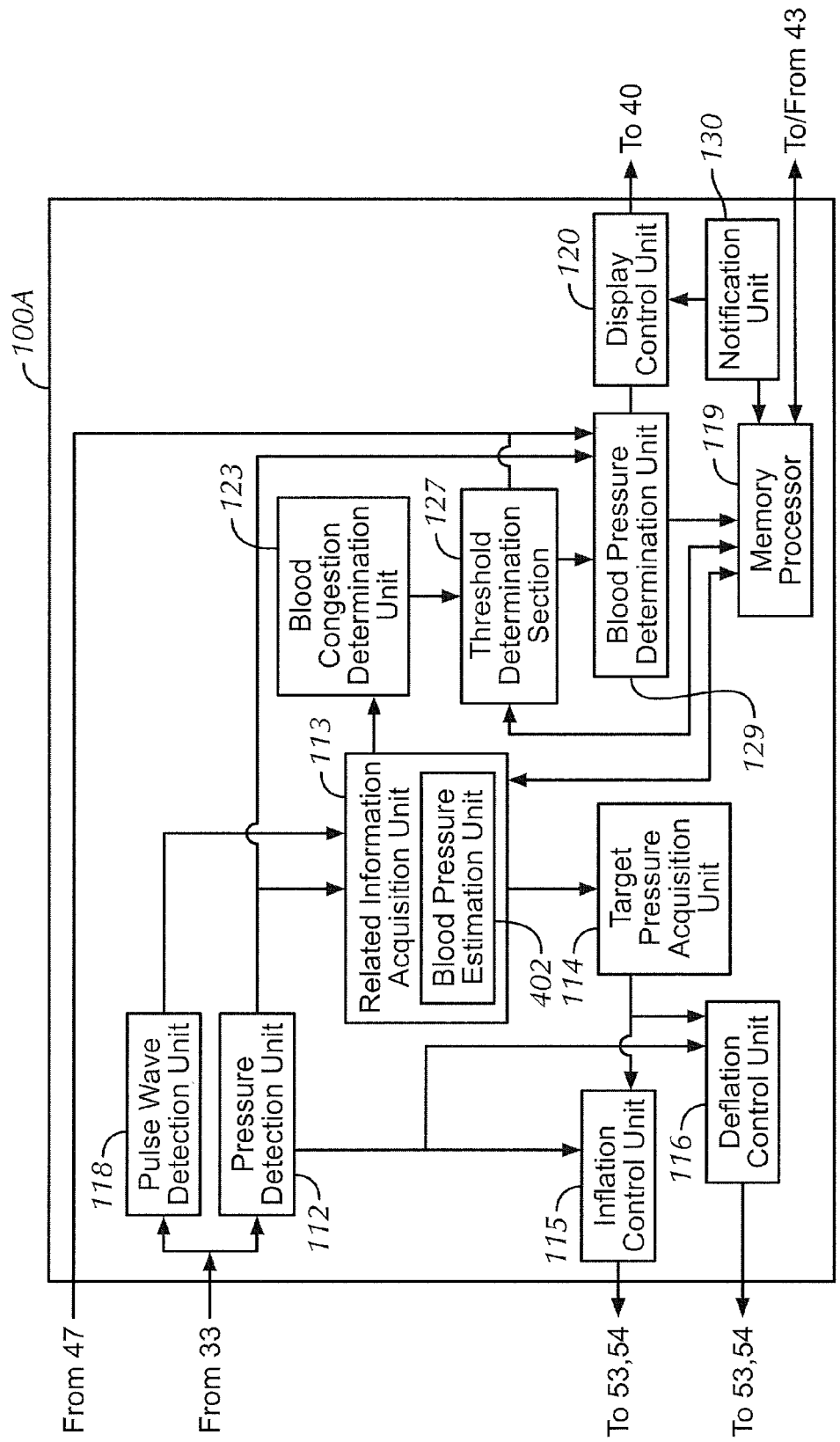
FIG. 10 is a functional configuration diagram of an electronic sphygmomanometer according to another embodiment of the present invention.

FIG. 10 is a function block diagram illustrating a function configuration of the electronic sphygmomanometer 1A. Referencing FIG. 10, different points from the configuration of FIG. 3 of the CPU 100A will be explained.

The CPU 100A is provided with a threshold determination section 127 in place of the parameter determination section 125, and is provided with a blood pressure determination unit 129 in place of the blood pressure calculation unit 117 as the blood pressure acquisition unit for acquiring blood pressure. Other configurations of FIG. 10 are similar to that explained in FIG. 3, and therefore descriptions thereof will be omitted.

In this embodiment, a threshold value TK is used to indicate a reference voltage for determining blood pressure based on the sound pressure of Korotkoff sounds, that is, based on the output voltage of the A/D converting circuit 47. The threshold value TK is stored in a predetermined area of the flash memory 43 in advance as an initial value.

In other words, with the microphone method as described above, the cuff pressure detected at the time that the Korotkoff sounds appear during the decompression process determines the systolic pressure, and the cuff pressure detected at the time when the Korotkoff sounds weaken or disappear determines the diastolic pressure.

The threshold value TK indicates a parameter value used to detect the appearance and weakening (disappearance) of Korotkoff sounds. The threshold value TK is determined by the threshold determination section 127 based on the determined degree of blood congestion. Therefore, the threshold determination section 127 corresponds to the parameter detection section for determining the parameter value used to determine blood pressure by the blood pressure determining unit 129.

Figure 11:
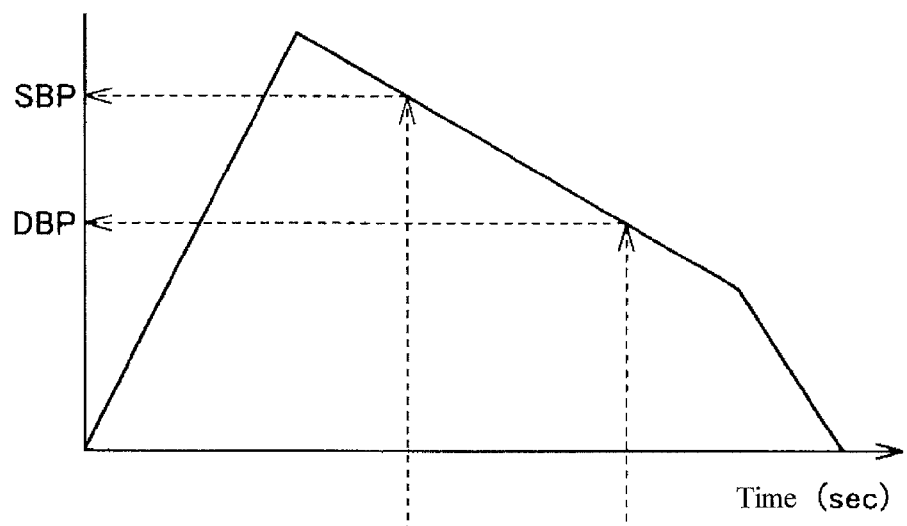
FIG. 11 is a graph for explaining changes in threshold value due to the presence or absence of blood congestion according to another embodiment of the present invention.
Figure 11:
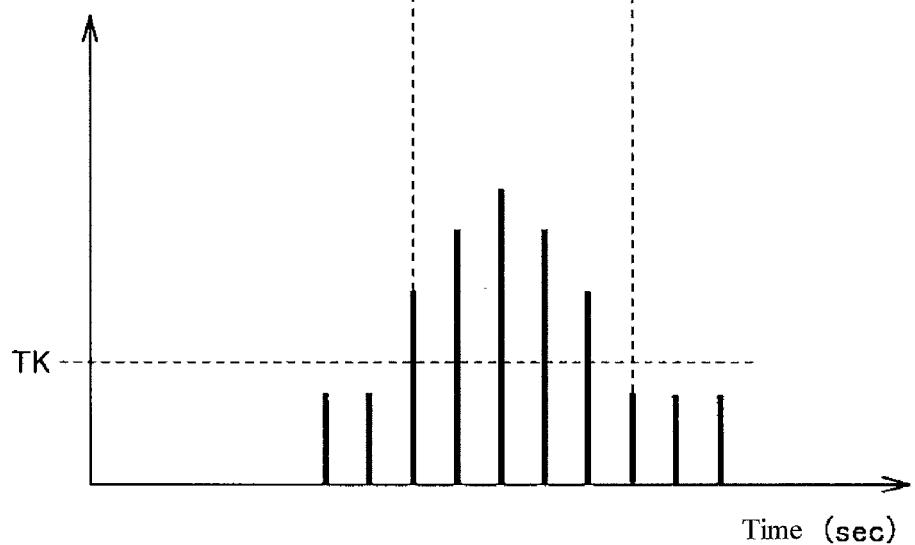
Figure 12:
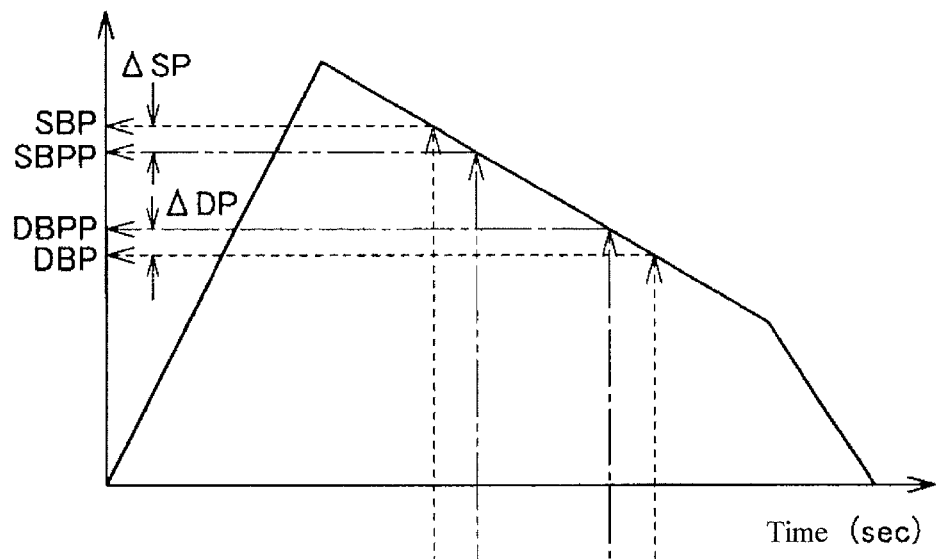
FIG. 12 is a graph for explaining changes in threshold value due to the presence or absence of blood congestion according to another embodiment of the present invention.
Figure 12:
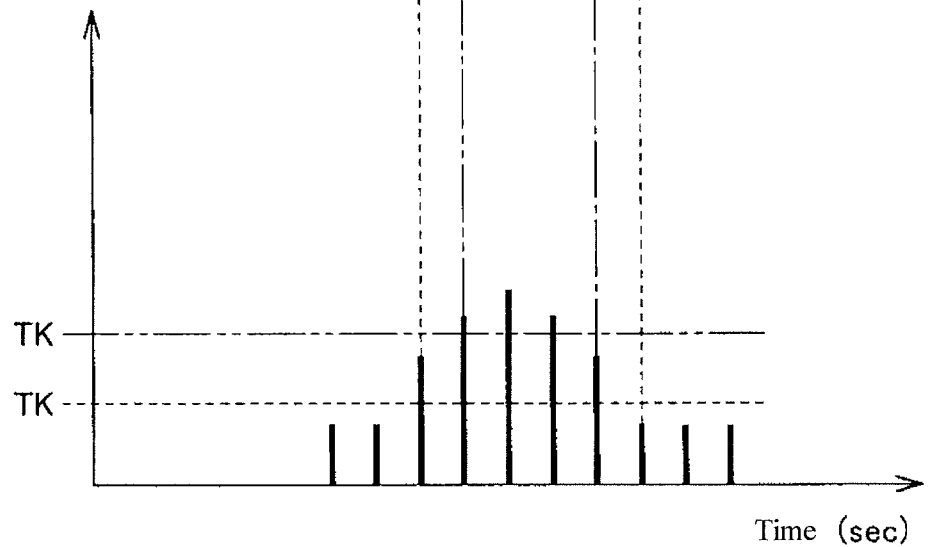

FIGS. 11 and 12 are graphs for explaining changes in the threshold value TK according to the existence or absence of blood congestion according to another embodiment of the present invention, and have been obtained by experiments by the inventors. Referencing FIGS. 11 and 12, the top graph is schematically illustrated to show changes in cuff pressure according to a pressure regulator at the time of blood pressure measurement. The passage of time (unit: sec) is recorded on the vertical axis of the graph, and cuff pressure (unit: mmHg) is recorded on the horizontal axis. Further, the bottom graph is schematically illustrated to show changes in the Korotkoff sound level (sound pressure level) associated with the top graph. Korotkoff sound levels detected in conjunction with changes in cuff pressure by a cuff regulator at the time of blood pressure measurement indicated by the top graph (in other words, output voltage values of the A/D converting circuit 47) are recorded on the vertical axis of the graph, and the passage of time (unit: sec) is recorded on the horizontal axis. Threshold value TK is illustrated in the bottom graph.

At the time of blood pressure measurement, the blood pressure determination unit 129 inputs the output voltage of the A/D converting circuit 47 after starting deflation until deflation ends (or until it is determined that blood pressure measurement has completed), and the input voltage value is compared to the predetermined threshold value TK, and based on the comparison result is determined whether the conditions are met (voltage value>threshold value TK). When it is determined that the initial conditions have been met after decompression starts, the cuff pressure detected by the pressure detection unit 112 determines the systolic blood pressure SBP, and immediately prior to determining that the conditions thereafter have not been met, the cuff pressure detected by the pressure detection unit 112 determine the diastolic blood pressure DBP.

Here, the blood pressure determining unit 129 synchronizes the cuff pressure from the pressure detection unit 112 with the output voltage from the A/D converting circuit 47 and inputs. At the time of each input, the data for the input cuff pressure and the data for the output voltage are associated and stored in the flash memory 43 via the memory processor 119. Therefore, the blood-pressure determining unit 129 can output the associated cuff pressures, that is, the systolic blood pressure SBP and the diastolic blood pressure DBP, by searching the flash memory 43 based on the output voltage at the time that the conditions described above were met or not met.

FIGS. 11 and 12 indicate graphs of when blood congestion has occurred and for when blood congestion has not occurred for the same patient. When determining blood pressure by using the threshold value TK, the determined blood pressures (systolic blood pressure SBP and diastolic blood pressure DBP) for a case in which blood congestion has not occurred in FIG. 11 and the determined blood pressures (systolic blood pressure SBPP and the diastolic blood pressure DBPP) of the case where blood congestion has occurred in FIG. 12, do not match. In other words, when blood congestion has occurred caused by reduced blood flow due to congestion causing the Korotkoff sounds to be smaller, and the same threshold value TK as the case when blood congestion has not occurred is used, the determined blood pressure includes the errors ΔSP and ΔDP (see FIG. 12). Correcting these errors requires that the threshold value TK illustrated by the dual dotted line in FIG. 12 change to the threshold value TK of the broken line (see FIG. 12).

The inventors determined the threshold value TK for each blood congestion by experiment in order to determine accurate blood pressure without relying on the degree of blood congestion. The table 432, having a plurality of various degrees of blood congestion as well as threshold values TK that correspond to various degrees of recorded blood congestion, is stored in advance in the flash memory 43. Therefore, the threshold determination section 127 reads corresponding threshold values TK by searching the table 432 via the memory processor 119 based on the determined degree of blood congestion according to the blood congestion determination unit 123, and outputs to the blood-pressure determination unit 129. In this manner, the blood pressure determination unit 129 can acquire threshold values TK to accurately measure blood pressure regardless of the degree of blood congestion.

(Process Flowchart)

A measurement operation according to a microphone method will be explained hereinafter according to the flowcharts in FIGS. 13 and 14. A program according to these flowcharts is stored in a memory unit 42 in advance. The CPU 100A reads commands of the program from the memory unit 42 and executes a measurement operation by controlling the operations of each section according to these commands.

Figure 13:
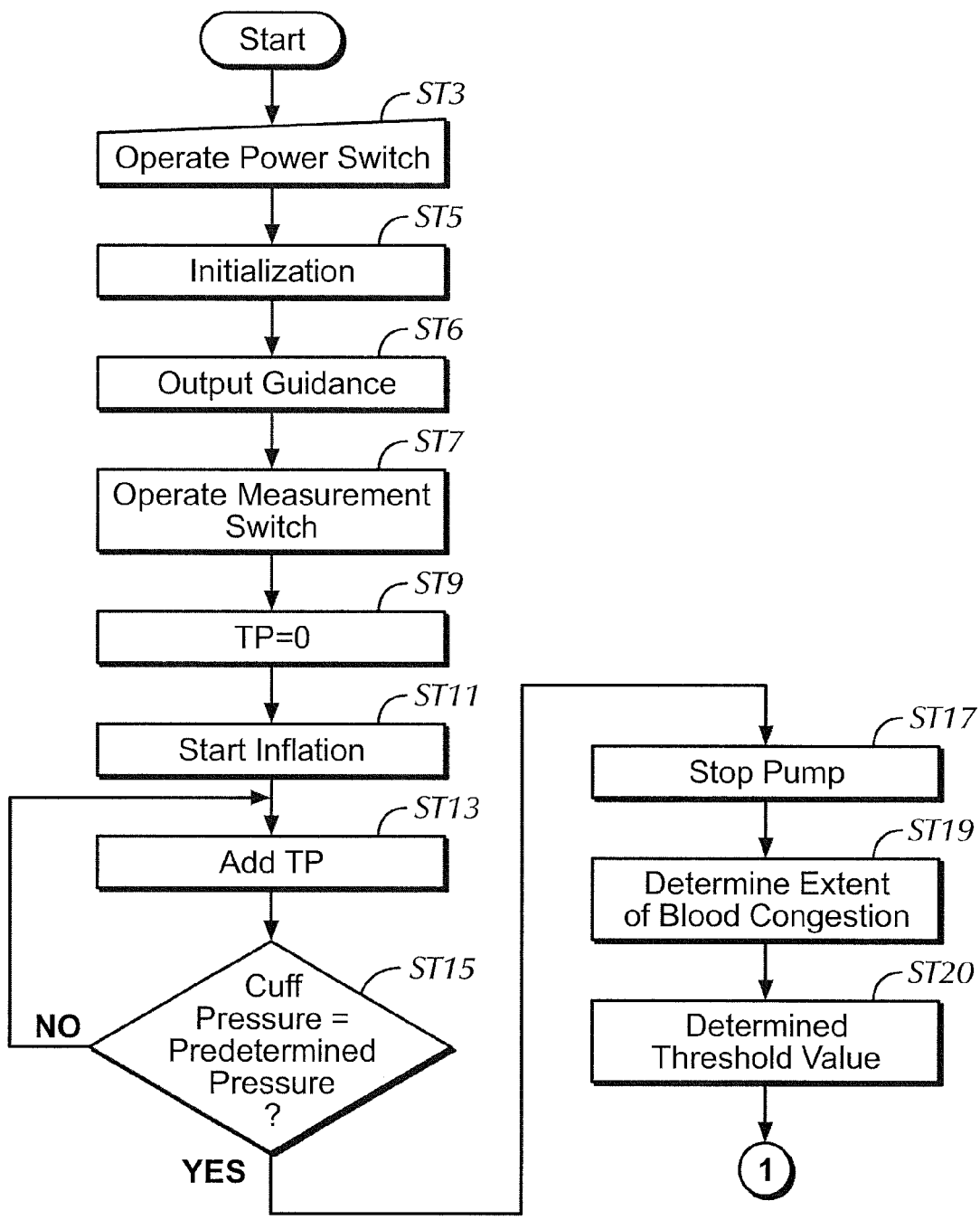
FIG. 13 is a process flowchart according to another embodiment of the present invention.

In the flowchart of FIG. 13, a process similar to that in steps ST 3 to ST 19 of FIG. 8 is executed in steps ST 3 to ST 19. The degree of blood congestion is determined by the blood congestion determination unit 123 accordingly.

Next, the threshold determination unit 127 inputs the degree of blood congestion determined from the blood congestion determination unit 123, searches the table 432 based on the input degree of blood congestion, and, according to the search, determines the threshold value TK that corresponds to the degree of blood congestion (ST 20).

Figure 14:
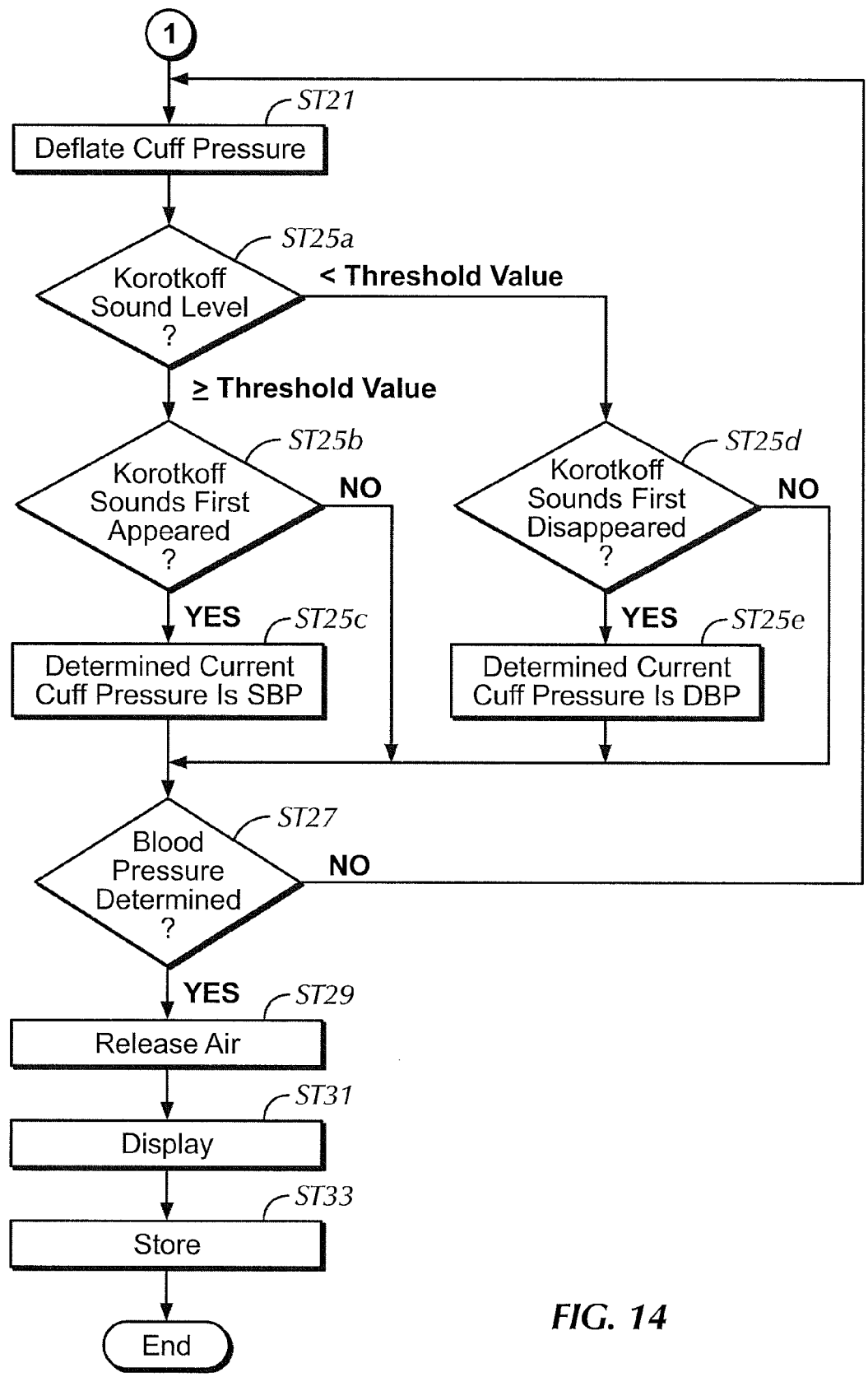
FIG. 14 is a process flowchart according to another embodiment of the present invention.

Referencing FIG. 14, the deflation control unit 116 gradually opens the valve 52 while the pump 51 is in a stopped state and begins deflation of the cuff pressure (ST 21). From hereafter, the description will transition to the deflation process.

In the deflation process, the blood pressure determination unit 129 compares the determined threshold value TK to the voltage value sequentially input from the A/D converting circuit 47, and based on the comparison result, the blood pressure determination unit 129 determines whether the conditions of (voltage value≥Threshold value TK) have been met (ST 25a). Based on the determined result, when it is determined that the initial conditions have been met after decompression starts (Yes at ST 25b), the cuff pressure detected by the pressure detection unit 112 determines the systolic blood pressure SBP (ST 25c), and then, immediately prior to first determining that the conditions have not been met (Yes at ST 25d), the cuff pressure detected by the pressure detection unit 112 determine the diastolic blood pressure DBP (ST 25e). While the blood pressure is not yet determined (No at ST 25b and No at ST 25d), the process moves to step ST 27.

According to the CPU 100A, it is determined whether both the systolic blood pressure SBP and the diastolic blood pressure DBP have been determined (ST 27). If it is determined that it has not been determined (No at ST 27), the process moves to step ST 21 and deflation continues, but if it is determined that both blood pressures have been determined (Yes at ST 27), the air within the cuff is rapidly deflated (ST 29), and the determined blood pressure values are displayed (ST 31). In addition, the memory processor 119 stores and associates the determined blood pressure values and pulse rate 427, the measured date and time 421, and the degree of blood congestion 422, and the like in the table 431 (ST 33). Thereafter, the CPU 100A ends the measurement process by turning off the power source 44.

With the oscillometric method and the microphone method described above, deflation blood pressure measurement methods were described to calculate blood pressure during the decompression process of cuff pressure, but similar procedures may also be applied to inflation blood pressure measurement methods to calculate blood pressure according to Korotkoff sounds or pressure pulse wave amplitude detected in the inflation process of cuff pressure. In this embodiment, the inflation speed in the inflation blood pressure measurement method can be set to the speed that is sufficiently slow (for example, 5.5 mmHg/sec) so as to enable sufficient pressure pulse wave amplitude information and Korotkoff sounds to be obtained even in people having a faint pulse rate. But for patients having a high systolic blood pressure, or patients having a long measurement location circumference length when wrapping the cuff 20, the degree of blood congestion becomes larger compared to a person having a low systolic blood pressure or a short measurement location circumference length.

To be able to address this, in one or more embodiments of the present invention, the degree of blood congestion is determined and blood-pressure is calculated using parameter values determined based on the degree of blood pressure congestion, or blood-pressure is determined using a threshold value TK determined based on the degree of blood pressure congestion. Therefore, for either measurement method accurate blood pressure can be measured regardless of how high or low the degree of blood congestion or the existence or absence of blood congestion.

(Effect of the Embodiments)

The effects achieved by the blood pressure measurement according to the oscillometric method and the microphone method according to the embodiments described above will be explained in comparison to conventional measurement methods.

In conventional blood pressure measurement, because it is necessary to increase cuff pressure to a predetermined pressure (for example, about systolic blood pressure+30 mmHg), inflation takes time for a person who has high blood pressure when inflating at a constant rate, while there is a tendency for blood congestion to easily occur in people having low blood pressure. Therefore, measurement errors due to blood congestion occur. In contrast to this, according to one or more embodiments of the present invention, the degree of blood congestion is determined in blood pressure measurement. Therefore, errors due to blood congestion can be eliminated during blood pressure measurement.

In addition, inflation speed is also influenced by air capacity in the cuff 20, that is, the measurement location circumference length. It is clear that transferring cuff pressure to the artery under the measurement location without attenuation requires that the width of the cuff 20 be no less than two-thirds of the measurement location circumference length. Therefore, the width of the cuff 20, that is, the quantity of air required to raise the cuff pressure, must increase in conjunction with the size of the measurement location circumference length. As a result, inflation speed slows having a tendency for blood congestion to easily occur. In order to address this, conventionally, the drive voltage of the pump used to inflate cuff pressure has been set higher to accommodate larger measurement location circumference lengths. However, in the electronic sphygmomanometers for home use, the size of the pump mounted therein is limited due to limitations in the size of the main body. Therefore, there has not been a sufficient remedy due to the limitations in inflation performance and also limitations in drive voltage of pumps that use common batteries as a drive power source. In contrast to this, according to one or more embodiments of the present invention, because the degree of blood congestion is determined in blood pressure measurement, errors due to blood congestion can be eliminated during blood pressure measurement without pump improvements and without excess power consumption.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A blood pressure measurement device comprising:
a cuff for wrapping around a measurement location of an arm of a patient;
a pressure sensor connected to the cuff that detects a cuff pressure and pulse waves that are superimposed on the cuff pressure;
a central processing unit (CPU) stored in a body of the device, the CPU comprising:
an inflation control unit that controls inflation of the cuff;
a deflation control unit that controls deflation of the cuff;
a blood pressure calculation unit that calculates a provisional blood pressure value of the patient based on the cuff pressure and pulse waves detected by the pressure sensor;
a blood congestion determination section that determines a degree of blood congestion having occurred at a peripheral side of the measurement location due to the cuff pressure on the measurement location,
wherein the blood pressure calculation unit further calculates a corrected blood pressure value based on the degree of the blood congestion; and
a parameter determination section that determines a parameter for correcting the provisional blood pressure value based on the degree of blood congestion, wherein the blood pressure calculation unit calculates the corrected blood pressure value based on the degree of blood congestion by correcting the provisional blood pressure value based on the parameter determined by the parameter determination section; and
a display that displays the corrected blood pressure value, wherein the blood congestion determination section determines the degree of blood congestion based on a time required for inflating the cuff.

2. A blood pressure measurement device comprising:
a cuff for wrapping around a measurement location of an arm of a patient;
a pressure sensor connected to the cuff that detects a cuff pressure and pulse waves that are superimposed on the cuff pressure;
a central processing unit (CPU) stored in a body of the device, the CPU comprising:
an inflation control unit that controls inflation of the cuff;
a deflation control unit that controls deflation of the cuff;
a blood pressure calculation unit that calculates a provisional blood pressure value of the patient based on the cuff pressure and pulse waves detected by the pressure sensor;
a blood congestion determination section that determines a degree of blood congestion having occurred at a peripheral side of the measurement location due to the cuff pressure on the measurement location,
wherein the blood pressure calculation unit further calculates a corrected blood pressure value based on the degree of the blood congestion; and
a parameter determination section that determines a parameter for correcting the provisional blood pressure value based on the degree of blood congestion, wherein the blood pressure calculation unit calculates the corrected blood pressure value based on the degree of blood congestion by correcting the provisional blood pressure value based on the parameter determined by the parameter determination section; and
a display that displays the corrected blood pressure value, wherein the blood congestion determination section determines the degree of blood congestion based on either one of an inflation speed of the cuff and a maximum cuff pressure of the cuff.

* * * * *